US008597510B2

(12) United States Patent
Yang

(10) Patent No.: US 8,597,510 B2
(45) Date of Patent: Dec. 3, 2013

(54) DEVICE OF MAGNETICALLY SEPARATING A SAMPLE

(75) Inventor: Shieh-Yueh Yang, Taipei County (TW)

(73) Assignee: Magqu Co. Ltd., Taipei County (TW)

( * ) Notice: Subject to any disclaimer, the term of this patent is extended or adjusted under 35 U.S.C. 154(b) by 274 days.

(21) Appl. No.: 12/910,099

(22) Filed: Oct. 22, 2010

(65) Prior Publication Data

US 2011/0100891 A1 May 5, 2011

(30) Foreign Application Priority Data

Oct. 30, 2009 (TW) ............................... 98220145 U

(51) Int. Cl.
*B03C 1/02* (2006.01)
*B01D 35/06* (2006.01)
*G01N 33/53* (2006.01)

(52) U.S. Cl.
USPC ........... 210/222; 210/232; 210/695; 436/526; 422/400; 422/549

(58) Field of Classification Search
USPC ........... 436/526; 422/400, 549; 210/695, 222, 210/232
See application file for complete search history.

(56) References Cited

U.S. PATENT DOCUMENTS 5,779,907 A * 7/1998 Yu ................................. 210/222
2009/0324451 A1 * 12/2009 Yin et al. ...................... 422/400

* cited by examiner

*Primary Examiner* — David A Reifsnyder
(74) *Attorney, Agent, or Firm* — WPAT, P.C.; Anthony King

(57) ABSTRACT

Present invention relates to a device magnetically separating a sample. The preferred material for the device is plastic. The device is a cuboid plate, which consists of one or two bottom sides and at least two lateral sides. The bottom side has wells on it to accommodate magnetic elements, and the magnetic element which is suitable to be accommodated into the wells comprising column shape, half-column shape, or half circular column shape magnetic elements. The magnetic element comprises permanent magnet or electromagnet, and the permanent magnet is selected from the group consisting of alnico, samarium cobalt, neodymium iron boron, or magnetic ceramic materials. The magnetic elements can adsorb the magnetic samples in the micro plate.

8 Claims, 5 Drawing Sheets

DEVICE OF MAGNETICALLY SEPARATING A SAMPLE

FIELD OF THE INVENTION

Present invention relates to a device magnetically separating a sample. The device is a cuboid plate, which consists of one or two bottom sides and at least two lateral sides. The bottom side has wells on it to accommodate magnetic elements. The magnetic elements can adsorb the magnetic samples in the micro plate.

BACKGROUND OF THE INVENTION

Microplate is a flat plate, which has lots of arranged equal size wells, and is suitable to contain the testing solution which is held in different wells in the plate to be analyzed. The microplate usually has several different sizes, 6, 12, 24, 48, 96, or 108 wells, can be used in various ways, like enzyme-linked immunosorbent assay (ELISA) or cell culture, etc. Therefore, microplate has been the standard tool or equipment for biological experiments.

However, the sample should be taken out from the microplate to do the separation procedure by high performance liquid chromatography (HPLC), and the sample will be under risks of contamination due to the complex procedure.

SUMMARY OF THE INVENTION

It has been well known that if user wants to separate the sample in the microplate, the sample should be taken out from the microplate to be separated by high performance liquid chromatography. The sample is under the risk of contamination due to the complex HPLC separation procedure. The present invention relates to a device magnetically separating a sample, which device has magnetic elements accommodated on the bottom of the plate. The magnetic sample can be adsorbed by the magnetic elements in the microplate, and the HPLC separation process can be waived to reduce the risk of sample contamination. An iron plate is used to fix the magnetic element to the microplate by magnetic adsorption force, preventing the magnetic elements pump out of the microplate due to the repulsion force among the magnetic elements.

Present invention provides a device magnetically separating a sample. The preferred material for the device is plastic. The device is a cuboid plate, which consists of one or two bottom sides and at least two lateral sides. The bottom side has wells on it to accommodate magnetic elements, and the magnetic element which is suitable to be accommodated into the wells comprising column shape, half-column shape, or half circular column shape magnetic elements. The magnetic element comprises permanent magnet or electromagnet, and the permanent magnet is selected from the group consisting of alnico, samarium cobalt, neodymium iron boron, or magnetic ceramic materials. The magnetic elements can adsorb the magnetic samples in the microplate.

DETAILED DESCRIPTION OF THE INVENTION

Present invention provides a device for magnetically separating a magnetic bead-based sample. The device comprises a microplate, comprising in grid a first plurality of wells, each for receiving the bead-based sample; a cuboid plate, located below the microplate and comprising in grid a second plurality of wells corresponding to the first plurality of wells, each of the second plurality of wells comprising a magnetic element to attract a corresponding bead-based sample; and a magnetic plate, being located below the cuboid plate for fixing a plurality of magnetic elements thereon. The magnetic elements are allocated in column shape, half-column shape, or half circular column shape. The magnetic elements are permanent magnets or electromagnets, and the permanent magnets are selected from the group consisting of alnico, samarium cobalt, neodymium iron boron, or magnetic ceramic materials. The magnetic elements can attract the magnetic bead-based samples in the microplate.

The upper lateral side of the cuboid plate of this invention matches the lower lateral side of the microplate, and the lower lateral side of the cuboid plate matches a magnetic plate, which is an iron plate and can be used to fix the magnetic element to the microplate by magnetic adsorption force.

The preferred material of the cuboid plate and the microplate used in present invention is plastic. The first plurality of wells and the second plurality of wells (column shape or cuboid shape; 6, 12, 24, 96, 108 wells can be used) are arranged in grid to contain the sample and the magnetic elements respectively.

The lower lateral side of the microplate and the upper lateral side of the cuboid plate can be designed to include a latch respectively for the microplate and the cuboid plate to easily match each other. The arrangement of the wells in the cuboid plate can be designed upon request, which means the well in the cuboid plate is not necessary to be precisely corresponding to the microplate. Moreover, a corner on the microplate and the cuboid plate can also be cut for easily identifying the direction of the plate.

EXAMPLE

Figure 1:
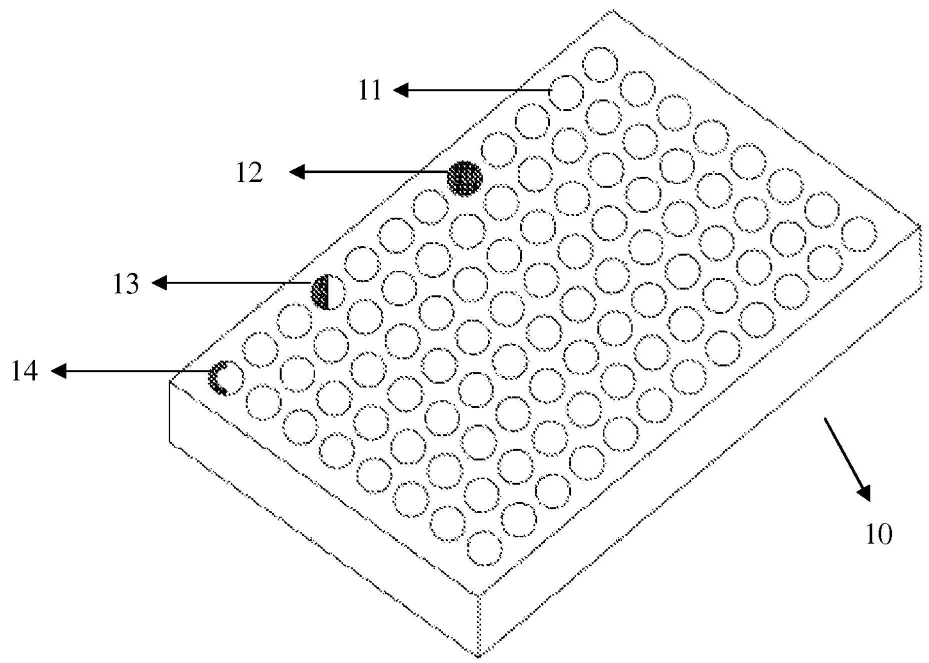
FIG. 1 shows one of the embodiments of present invention. Cuboid plate (10), well (11), column shape permanent magnet (12), half-column shape permanent magnet (13), half circular column shape permanent magnet (14).
Figure 2:
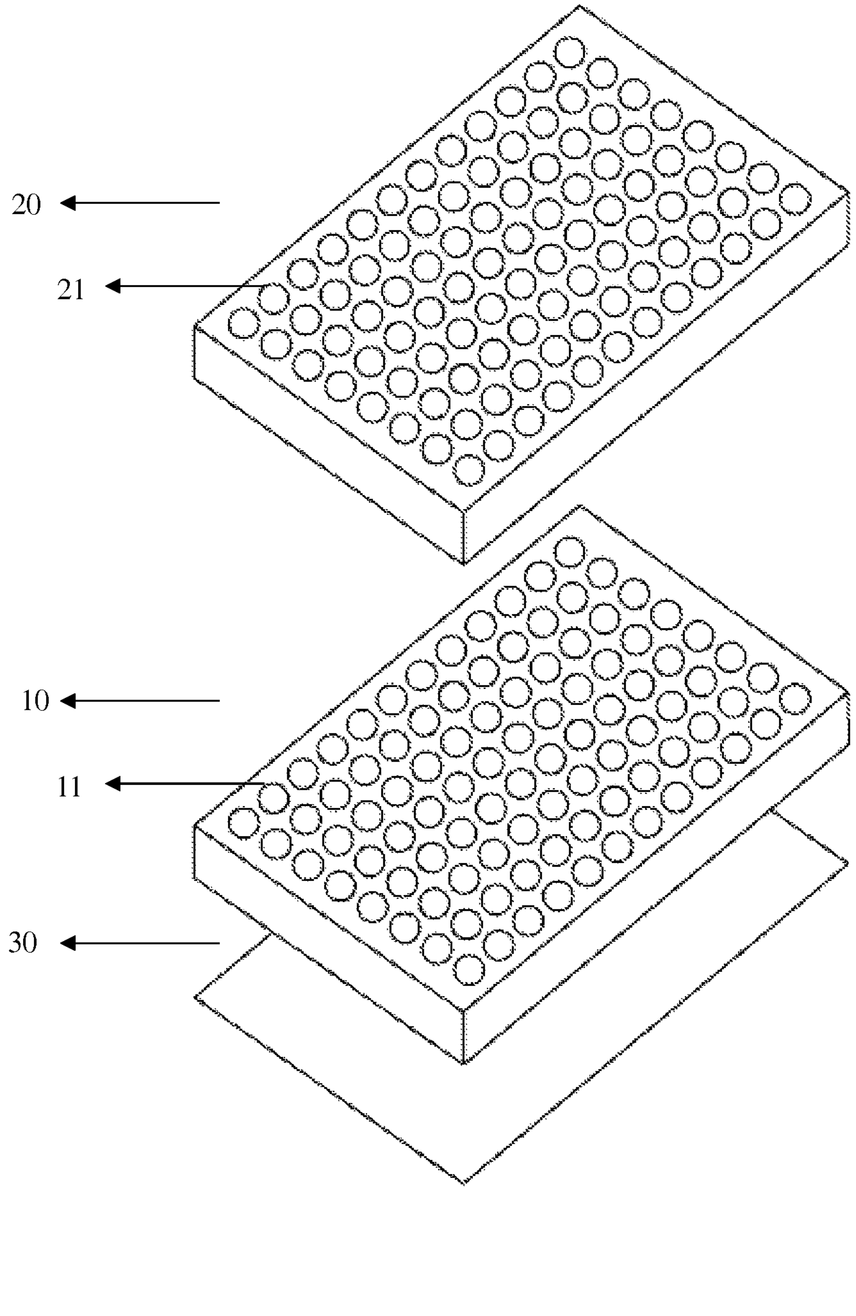
FIG. 2 shows an embodiment of present invention. Cuboid plate (10), well (11), microplate (20), well (21), magnetic plate (30).

As shown in FIG. 1, a cuboid plate (10) had wells (11) to accommodate column permanent magnet (12), half column permanent magnet (13), or half circular column permanent magnet (14). FIG. 2 showed that by matching present invention to the microplate (20), sample in the well (21) can be adsorbed by present invention. The magnetic plate (30) was used to fix the permanent magnet to present invention to prevent rotation of the permanent magnet, which would cause the permanent magnet to pump out of the cuboid plate due to the repulsion force of magnet.

Figure 3:
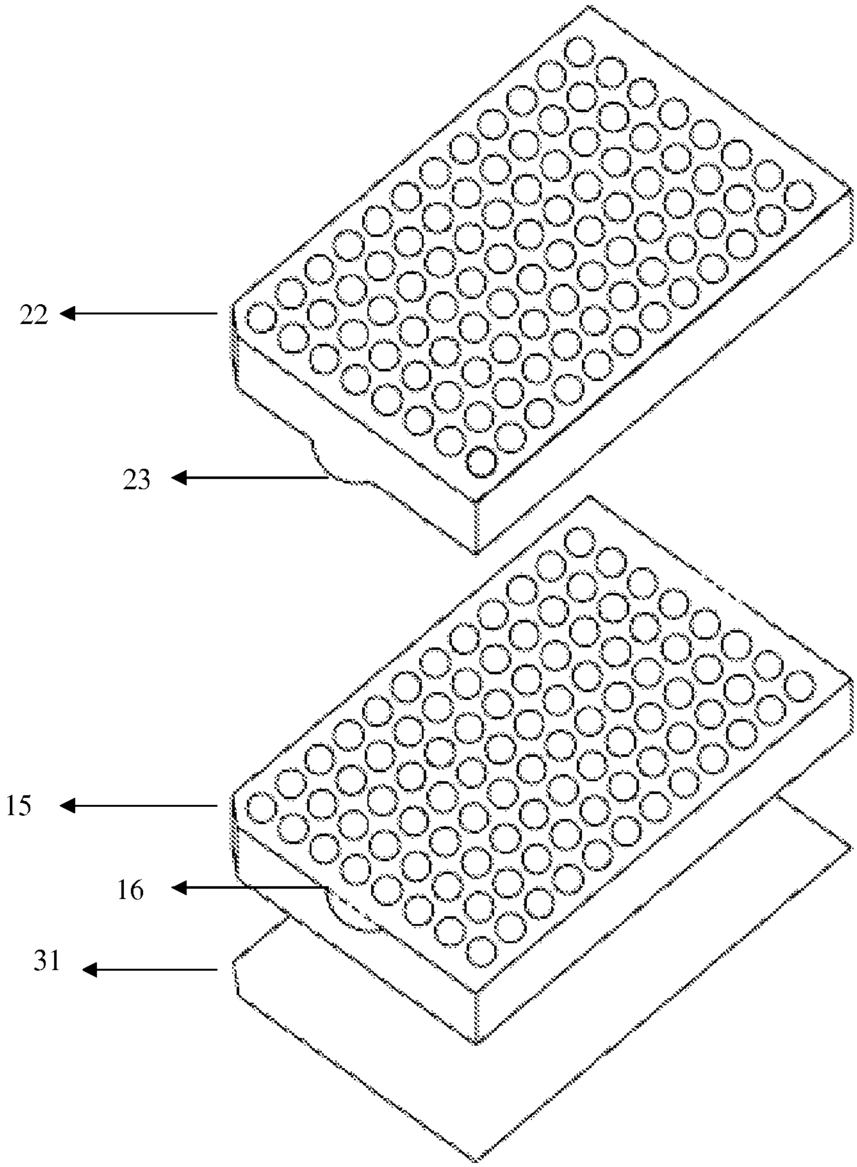
FIG. 3 shows a preferred embodiment of present invention. Facet (15), latch (16), facet (22), latch (23), facet (31).

FIG. 3 showed an embodiment based on FIG. 2. A facet (15, 22, 31) was designed to identify the direction of the plate. There was a latch (16, 23) designed on the lower lateral side of microplate and the upper lateral side of present invention, respectively, and the latches on microplate and present invention can match each other as well.

Figure 4:
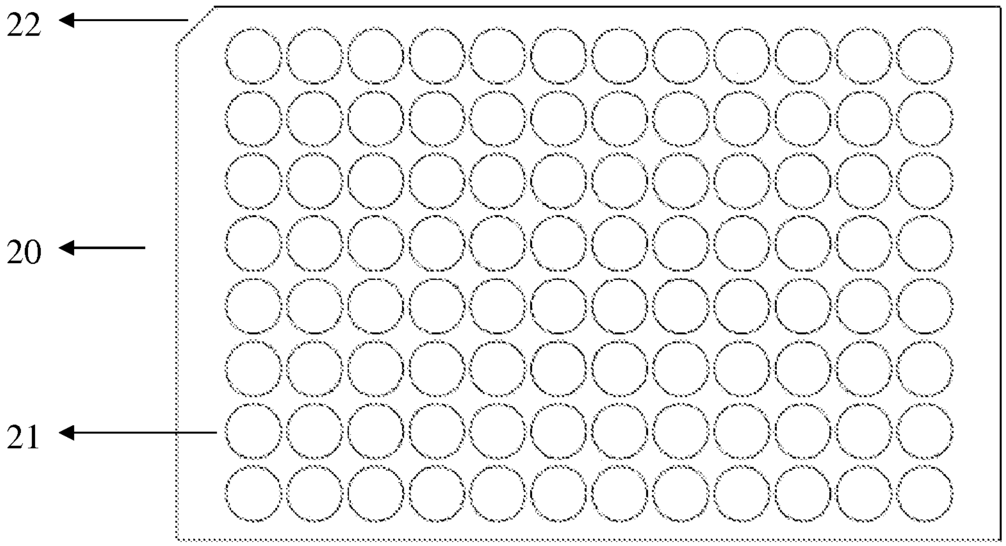
FIG. 4 shows the top view of 96 wells microplate. Microplate (20), well (21), facet (22).
Figure 5:
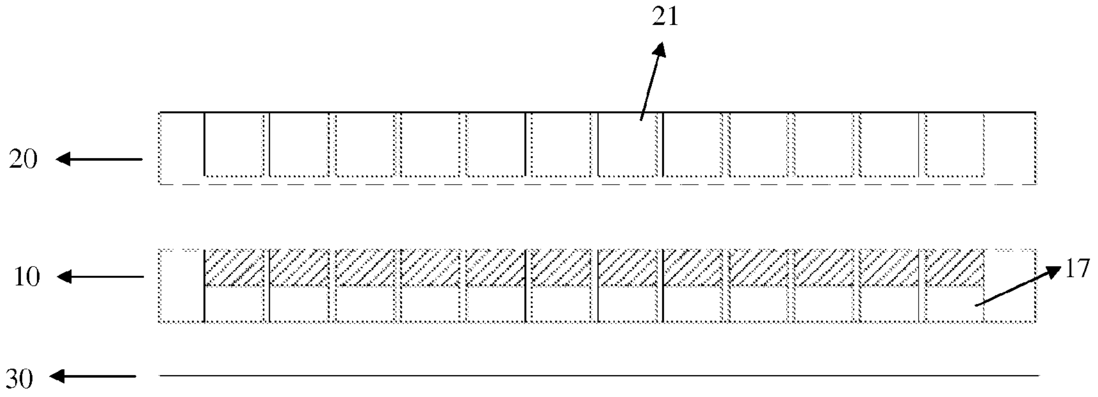
FIG. 5 shows a sectional view of FIG. 1. Cuboid plate (10), permanent magnet (17), microplate (20), well (21), magnetic plate (30).

FIG. 4 was the top view of microplate of present invention. FIG. 5 was the sectional view of FIG. 1, and the FIG. 5 was consisted of present invention, microplate, and an iron plate; the permanent magnet (17) was placed in present invention to adsorb the magnetic sample in the microplate.

What is claimed is:

1. A device for magnetically separating a magnetic bead-based sample, comprising:

a microplate, comprising in grid a first plurality of wells, each for receiving the magnetic bead-based sample;

a cuboid plate, located below the microplate, comprising in grid a second plurality of wells corresponding to the first plurality of wells, each of the second plurality of wells comprising a magnetic element to attract the magnetic bead-based sample in the first plurality of wells correspondingly; and a magnetic plate, being located below the cuboid plate for fixing the plurality of magnetic elements thereon.

2. A device for magnetically separating a magnetic bead-based sample of claim 1, wherein the number of the first plurality of wells and the number of the corresponding second plurality of wells are 6, 12, 24, 48, 96, or 108.

3. A device for magnetically separating a magnetic bead-based sample of claim 1, wherein a corner on the cuboid plate and a corresponding corner of the microplate are cut to be able to identify direction.

4. A device for magnetically separating a magnetic bead-based sample of claim 1, wherein each of the first plurality of wells and the second plurality of wells is in a column shape or a cuboid shape.

5. A device for magnetically separating a magnetic bead-based sample of claim 1, wherein the cuboid plate is made of plastic.

6. A device for magnetically separating a magnetic bead-based sample of claim 1, wherein the magnetic element is a permanent magnet or an electromagnet.

7. A device for magnetically separating a magnetic bead-based sample of claim 6, wherein the permanent magnet is selected from a group consisting of alnico, samarium cobalt, neodymium iron boron, and magnetic ceramic materials.

8. A device for magnetically separating a magnetic bead-based sample of claim 1, wherein the magnetic plate is an iron plate.

* * * * *